United States Patent
Panjabi

(10) Patent No.: US 7,029,475 B2
(45) Date of Patent: Apr. 18, 2006

(54) SPINAL STABILIZATION METHOD

(75) Inventor: Manohar M. Panjabi, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 10/835,109

(22) Filed: Apr. 30, 2004

(65) Prior Publication Data

US 2004/0236329 A1      Nov. 25, 2004

Related U.S. Application Data

(60) Provisional application No. 60/506,724, filed on Sep. 30, 2003, provisional application No. 60/467,414, filed on May 2, 2003.

(51) Int. Cl.
*A61B 17/56*      (2006.01)

(52) U.S. Cl. ....................................................... 606/61

(58) Field of Classification Search .................. 606/61, 606/60; 623/17.11, 17.12, 17.13, 17.14, 623/17.15, 17.16; 128/898
See application file for complete search history.

(56) References Cited

U.S. PATENT DOCUMENTS

| | | | |
|---|---|---|---|
| 2,733,596 A | 2/1956 | Painter | |
| 4,328,960 A | 5/1982 | Handke et al. | |
| 4,352,514 A | 10/1982 | Orima | |
| 4,558,852 A | 12/1985 | Steiner et al. | |
| 4,650,167 A | 3/1987 | Steiner et al. | |
| 4,743,260 A | 5/1988 | Burton | |
| 4,759,769 A * | 7/1988 | Hedman et al. | 623/17.13 |
| 5,034,011 A | 7/1991 | Howland | |
| 5,174,551 A | 12/1992 | Mintgen | |
| 5,180,393 A | 1/1993 | Commarmond | |
| 5,291,901 A | 3/1994 | Graf | |
| 5,329,933 A | 7/1994 | Graf | |
| 5,375,823 A * | 12/1994 | Navas | 623/17.15 |
| 5,415,661 A | 5/1995 | Holmes | |
| 5,423,816 A | 6/1995 | Lin | |
| 5,480,401 A * | 1/1996 | Navas | 606/61 |
| 5,505,118 A | 4/1996 | Arnesen et al. | |
| 5,540,688 A | 7/1996 | Navas | |
| 5,562,737 A | 10/1996 | Graf | |
| 5,653,680 A | 8/1997 | Cruz | |
| 5,672,175 A | 9/1997 | Martin | |

(Continued)

FOREIGN PATENT DOCUMENTS

AU           654740 B           11/1994

(Continued)

OTHER PUBLICATIONS

Keller, Tony S. et al., "Force-deformation response of the lumbar spine: a sagittal plane model of . . . ", Clinical Biomechanics 17 (2002) 185-196.

(Continued)

*Primary Examiner*—Pedro Philogene
(74) *Attorney, Agent, or Firm*—McCarter & English, LLP

(57) ABSTRACT

A dynamic spine stabilizer moves under the control of spinal motion providing increased mechanical support within a central zone corresponding substantially to the neutral zone of the injured spine. The dynamic spine stabilizer includes a support assembly and a resistance assembly associated with the support assembly. The resistance assembly generates greater increase in mechanical force during movement within the central zone and lesser increase in mechanical force during movement beyond the central zone. A method for using the stabilizer is also disclosed.

19 Claims, 7 Drawing Sheets

U.S. PATENT DOCUMENTS

| | | |
|---|---|---|
| RE36,221 E | 6/1999 | Breard et al. |
| 5,961,516 A | 10/1999 | Graf |
| 6,149,655 A | 11/2000 | Constantz et al. |
| 6,162,223 A | 12/2000 | Orsak et al. |
| 6,176,860 B1 | 1/2001 | Howard |
| 6,241,730 B1 | 6/2001 | Alby |
| 6,267,764 B1 | 7/2001 | Elberg |
| 6,293,949 B1 | 9/2001 | Justis et al. |
| 6,375,681 B1 | 4/2002 | Truscott |
| 6,402,750 B1 | 6/2002 | Atkinson et al. |
| 6,419,706 B1 | 7/2002 | Graf |
| 6,440,169 B1 | 8/2002 | Elberg et al. |
| 6,508,818 B1 | 1/2003 | Steiner et al. |
| 6,554,831 B1 | 4/2003 | Rivard et al. |
| 6,645,207 B1 | 11/2003 | Dixon et al. |
| 6,749,614 B1 | 6/2004 | Teitelbaum et al. |
| 6,761,719 B1 * | 7/2004 | Justis et al. ............ 606/61 |
| 6,835,205 B1 * | 12/2004 | Atkinson et al. ........ 623/17.11 |
| 2002/0095154 A1 | 7/2002 | Atkinson et al. |
| 2002/0151978 A1 | 10/2002 | Zacouto et al. |
| 2003/0055427 A1 * | 3/2003 | Graf ........................ 606/61 |
| 2003/0171749 A1 | 9/2003 | Le Couedic et al. |
| 2003/0220642 A1 | 11/2003 | Freudiger |
| 2003/0220643 A1 | 11/2003 | Ferree |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0082954 A1 | 4/2004 | Teitelbaum et al. |
| 2004/0082961 A1 | 4/2004 | Teitelbaum |
| 2004/0087950 A1 | 5/2004 | Teitelbaum |
| 2004/0143264 A1 | 7/2004 | McAfee |
| 2004/0147928 A1 | 7/2004 | Landry et al. |
| 2004/0167523 A1 | 8/2004 | Jackson |

FOREIGN PATENT DOCUMENTS

| | | |
|---|---|---|
| AU | 199917670 B2 | 7/1999 |
| CA | 2135838 A | 5/1995 |
| CA | 2213058 | 2/1998 |
| EP | 654249 B1 | 3/1990 |
| EP | 0516567 | 12/1992 |
| EP | 534874 A1 | 3/1993 |
| EP | 0576379 | 12/1994 |
| EP | 654249 A1 | 5/1995 |
| EP | 0611554 | 1/1996 |
| EP | 0821917 | 2/1998 |
| EP | 1039855 | 10/2000 |
| FR | 2681520 A1 | 3/1993 |
| FR | 2692468 A1 | 12/1993 |
| FR | 2694182 | 2/1994 |
| FR | 2701651 | 8/1994 |
| FR | 2712482 A1 | 5/1995 |
| FR | 2701650 | 1/1996 |
| FR | 2751864 | 2/1998 |
| FR | 2676911 | 3/1998 |
| FR | 2772594 | 6/1999 |
| FR | 2775891 A1 | 9/1999 |
| FR | 2794362 A1 | 12/2000 |
| FR | 2799949 | 1/2001 |
| FR | 2801782 A1 | 6/2001 |
| FR | 2803188 A1 | 7/2001 |
| FR | 2809304 A1 | 11/2001 |
| FR | 2810873 A1 | 1/2002 |
| FR | 2812535 A1 | 2/2002 |
| FR | 2799949 | 4/2004 |
| GB | 2382304 | 10/2001 |
| GB | 2382304 | 5/2003 |
| JP | 3-256281 | 11/1991 |
| JP | 7-289562 | 11/1995 |
| JP | 6-285100 | 1/1996 |
| JP | 8191840 A | 7/1996 |
| JP | 10-71157 | 3/1998 |
| JP | 10-277070 | 10/1998 |
| KR | 236010 | 9/1999 |
| WO | WO 99/32054 | 7/1999 |
| WO | WO 00/74605 | 12/2000 |
| WO | WO 01/39678 | 6/2001 |
| WO | WO01/45576 | 6/2001 |
| WO | WO 01/45576 | 6/2001 |
| WO | WO 01/49192 | 7/2001 |
| WO | WO 02/00124 | 1/2002 |
| WO | WO 02/102259 | 12/2002 |
| WO | WO 03/007828 | 1/2003 |
| WO | WO 2004/024011 | 3/2004 |

OTHER PUBLICATIONS

Panjabi, The Stabilizing System of the Spine, Part I, Function, Dysfunction, Adaptation and Enhancement, Journal of Spinal Disorders, 1992, vol. 5, No. 4, pp. 383-389.

Panjabi, The Stabilizing System of the Spine, Part II, Neutral Zone and Instability Hypothesis, Journal of Spinal Disorders, 1992, vol. 5, No. 4, pp. 390-397.

* cited by examiner

*DSS in Tension*

*DSS in Compression*

SPINAL STABILIZATION METHOD

CROSS REFERENCE TO RELATED APPLICATIONS

This application is based upon U.S. Provisional Application Ser. No. 60/506,724, entitled "DYNAMIC SPINE STABILIZER", filed Sep. 30, 2003, and U.S. Provisional Patent Application Ser. No. 60/467,414, entitled "DYNAMIC SPINE STABILIZER", filed May 2, 2003.

BACKGROUND OF THE INVENTION

1. Field of the Invention

The invention relates to a method and apparatus for spinal stabilization. More particularly, the invention relates to a method and apparatus for applying increased incremental mechanical resistance when the spine moves within its neutral zone.

2. Description of the Prior Art

Low back pain is one of the most expensive diseases afflicting industrialized societies. With the exception of the common cold, it accounts for more doctor visits than any other ailment. The spectrum of low back pain is wide, ranging from periods of intense disabling pain which resolve, to varying degrees of chronic pain. The conservative treatments available for lower back pain include: cold packs, physical therapy, narcotics, steroids and chiropractic maneuvers. Once a patient has exhausted all conservative therapy, the surgical options range from micro discectomy, a relatively minor procedure to relieve pressure on the nerve root and spinal cord, to fusion, which takes away spinal motion at the level of pain.

Each year, over 200,000 patients undergo lumbar fusion surgery in the United States. While fusion is effective about seventy percent of the time, there are consequences even to these successful procedures, including a reduced range of motion and an increased load transfer to adjacent levels of the spine, which accelerates degeneration at those levels. Further, a significant number of back-pain patients, estimated to exceed seven million in the U.S., simply endure chronic low-back pain, rather than risk procedures that may not be appropriate or effective in alleviating their symptoms.

New treatment modalities, collectively called motion preservation devices, are currently being developed to address these limitations. Some promising therapies are in the form of nucleus, disc or facet replacements. Other motion preservation devices provide dynamic internal stabilization of the injured and/or degenerated spine, without removing any spinal tissues. A major goal of this concept is the stabilization of the spine to prevent pain while preserving near normal spinal function. The primary difference in the two types of motion preservation devices is that replacement devices are utilized with the goal of replacing degenerated anatomical structures which facilitates motion while dynamic internal stabilization devices are utilized with the goal of stabilizing and controlling abnormal spinal motion.

Over ten years ago a hypothesis of low back pain was presented in which the spinal system was conceptualized as consisting of the spinal column (vertebrae, discs and ligaments), the muscles surrounding the spinal column, and a neuromuscular control unit which helps stabilize the spine during various activities of daily living. Panjabi M M. "The stabilizing system of the spine. Part I. Function, dysfunction, adaptation, and enhancement." *J Spinal Disord* 5 (4): 383–389, 1992a. A corollary of this hypothesis was that strong spinal muscles are needed when a spine is injured or degenerated. This was especially true white standing in neutral posture. Panjabi M M. "The stabilizing system of the spine. Part II. Neutral zone and instability hypothesis." *J Spinal Disord* 5 (4): 390–397, 1992b. In other words, a low-back patient needs to have sufficient well-coordinated muscle forces, strengthening and training the muscles where necessary, so they provide maximum protection while standing in neutral posture.

Dynamic stabilization (non-fusion) devices need certain functionality in order to assist the compromised (injured or degenerated with diminished mechanical integrity) spine of a back patient. Specifically, the devices must provide mechanical assistance to the compromised spine, especially in the neutral zone where it is needed most. The "neutral zone" refers to a region of low spinal stiffness or the toe-region of the Moment-Rotation curve of the spinal segment (see FIG. 1). Panjabi M M, Goel V K, Takata K. 1981 Volvo Award in Biomechanics. "Physiological Strains in Lumbar Spinal Ligaments, an in vitro Biomechanical Study." *Spine* 7 (3): 192–203, 1982. The neutral zone is commonly defined as the central part of the range of motion around the neutral posture where the soft tissues of the spine and the facet joints provide least resistance to spinal motion. This concept is nicely visualized on a load-displacement or moment-rotation curve of an intact and injured spine as shown in FIG. 1. Notice that the curves are non-linear; that is, the spine mechanical properties change with the amount of angulations and/or rotation. If we consider curves on the positive and negative sides to represent spinal behavior in flexion and extension respectively, then the slope of the curve at each point represents spinal stiffness. As seen in FIG. 1, the neutral zone is the low stiffness region of the range of motion.

Experiments have shown that after an injury of the spinal column or due to degeneration, neutral zones, as well as ranges of motion, increase (see FIG. 1). However, the neutral zone increases to a greater extent than does the range of motion, when described as a percentage of the corresponding intact values. This implies that the neutral zone is a better measure of spinal injury and instability than the range of motion. Clinical studies have also found that the range of motion increase does not correlate well with low back pain. Therefore, the unstable spine needs to be stabilized especially in the neutral zone. Dynamic internal stabilization devices must be flexible so as to move with the spine, thus allowing the disc, the facet joints, and the ligaments normal physiological motion and loads necessary for maintaining their nutritional well-being. The devices must also accommodate the different physical characteristics of individual patients and anatomies to achieve a desired posture for each individual patient.

With the foregoing in mind, those skilled in the art will understand that a need exists for a spinal stabilization device which overcomes the shortcoming of prior art devices. The present invention provides such an apparatus and method for spinal stabilization.

SUMMARY OF THE INVENTION

It is, therefore, an object of the present invention to provide a method for spinal stabilization. The method is achieved by securing a dynamic stabilizer to vertebrae of a spine and providing mechanical assistance in the form of resistance to a region of the spine to which the dynamic stabilizer is attached. The resistance is applied such that greater mechanical assistance is provided while the spine is around its neutral zone and lesser mechanical assistance is provided while the spine bends beyond its neutral zone.

It is also an object of the present invention to provide a dynamic stabilizer that moves under the control of spinal motion providing increased mechanical support within a central zone corresponding substantially to a neutral zone of an injured spine. The stabilizer includes a support assembly and a resistance assembly associated with the support assembly. The resistance assembly generates resistance applying greater resistance to movement during movement within the central zone and lower resistance to movement while the stabilizer undergoes extended movement beyond its central zone.

It is another object of the present invention to provide a dynamic stabilizer including a piston assembly and a resistance assembly associated with the piston assembly. The resistance assembly is composed of a first spring and a second spring and the piston assembly is shaped and dimensioned or linking the resistance assembly to a boded member.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

With reference to FIGS. 2, 3a–c and 4, a method and apparatus are disclosed for spinal stabilization. In accordance ,with a preferred embodiment of the present invention, the spinal stabilization method is achieved by securing an internal dynamic spine stabilizer 10 between adjacent vertebrae 12, 14 and providing mechanical assistance in the form of elastic resistance to the region of the spine to which the dynamic spine stabilizer 10 is attached. The elastic resistance is applied as a function of displacement such that greater mechanical assistance is provided while the spine is in its neutral zone and lesser mechanical assistance is provided while the spine bends beyond its neutral zone. Although the term elastic resistance is used throughout the body of the present specification, other forms of resistance may be employed without departing from the spirit of the present invention.

Figure 2:
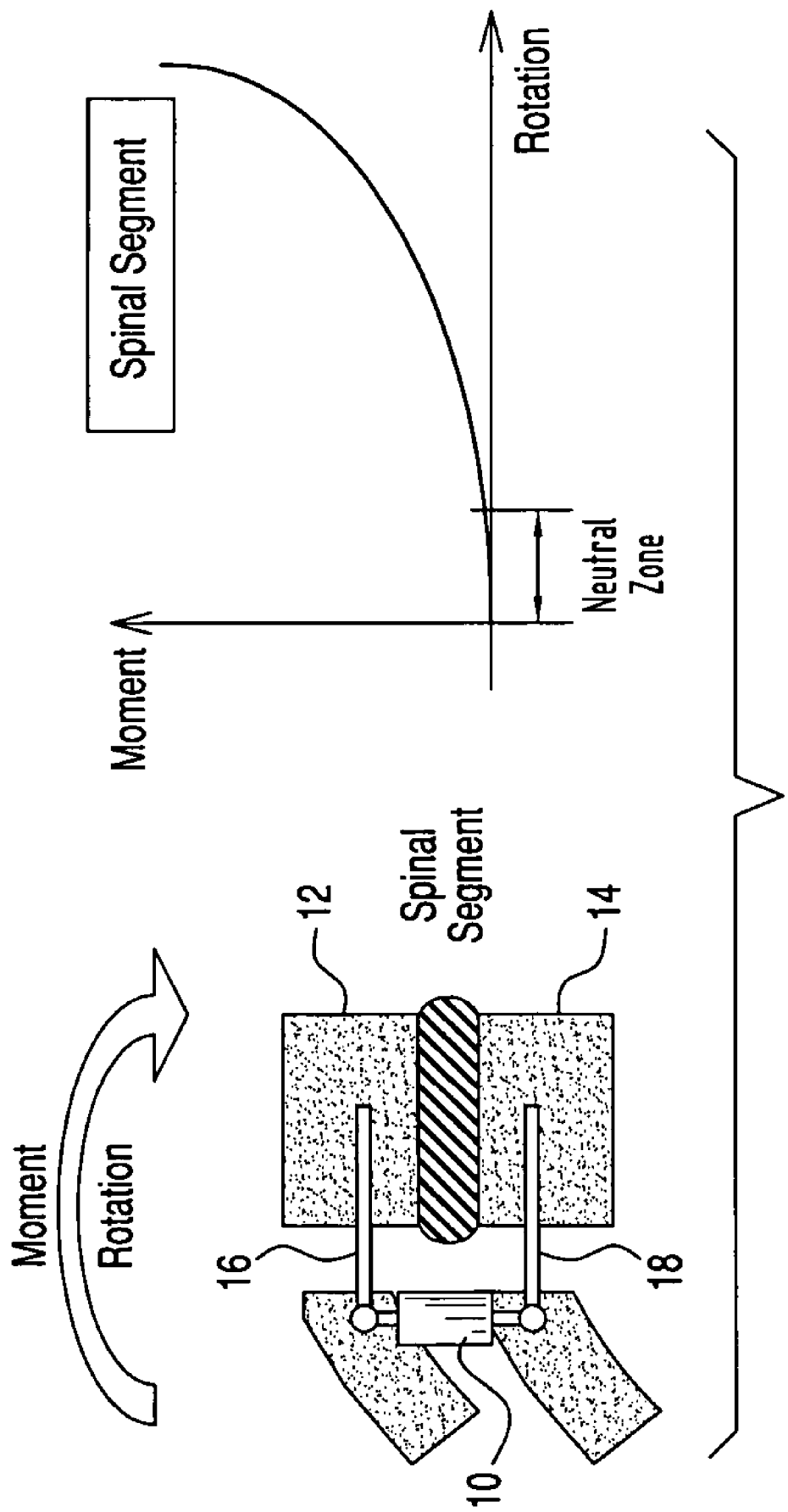
FIG. 2 is a schematic representation of a spinal segment in conjunction with a Moment-Rotation curve for a spinal segment, showing the low spinal stiffness within the neutral zone.

As those skilled in the art will certainly appreciate, and as mentioned above, the "neutral zone" is understood to refer to a region of low spinal stiffness or the toe-region of the Moment-Rotation curve of the spinal segment (see FIG. 2). That is, the neutral zone may be considered to refer to a region of laxity around the neutral resting position of a spinal segment where there is minimal resistance to intervertebral motion. The range of the neutral zone is considered to be of major significance in determining spinal stability. Panjabi, M M. "The stabilizing system of the spine. Part II. Neutral zone and instability hypothesis." *J Spinal Disorders* 1992; 5(4): 390–397.

In fact, the inventor has previously described the load displacement curve associated with spinal stability through the use of a "ball in a bowl" analogy. According to this analogy, the shape of the bowl indicates spinal stability. A deeper bowl represents a more stable spine, while a more shallow bowl represents a less stable spine. The inventor previously hypothesized that for someone without spinal injury there is a normal neutral zone (that part of the range of motion where there is minimal resistance to intervertebral motion) with a normal range of motion, and in turn, no spinal pain. In this instance, the bowl is not too deep nor too shallow. However, when an injury occurs to an anatomical structure, the neutral zone of the spinal column increases and the ball moves freely over a larger distance. By this analogy, the bowl would be more shallow and the ball less stable, and consequently, pain results from this enlarged neutral zone.

In general, pedicle screws 16, 18 attach the dynamic spine stabilizer 10 to the vertebrae 12, 14 of the spine using well-tolerated and familiar surgical procedures known to those skilled in the art. In accordance with a preferred embodiment, and as those skilled in the art will certainly appreciate, a pair of opposed stabilizers are commonly used to balance the loads applied to the spine (see FIG. 3c). The dynamic spine stabilizer 10 assists the compromised (injured and/or degenerated) spine of a back pain patient, and helps her/him perform daily activities. The dynamic spine stabilizer 10 does so by providing controlled resistance to spinal motion particularly around neutral posture in the region of neutral zone. As the spine bends forward (flexion) the stabilizer 10 is tensioned (see FIG. 3d) and when the spine bends backward (extension) the stabilizer 10 is compressed (see FIG. 3e).

The resistance to displacement provided by the dynamic spine stabilizer 10 is non-linear, being greatest in its central zone so as to correspond to the individual's neutral zone; that is, the central zone of the stabilizer 10 provides a high level of mechanical assistance in supporting the spine. As the individual moves beyond the neutral zone, the increase in resistance decreases to a more moderate level. As a result, the individual encounters greater resistance to movement (or greater incremental resistance) while moving within the neutral zone.

The central zone of the dynamic spine stabilizer 10, that is, the range of motion in which the spine stabilizer 10 provides the greatest resistance to movement, is adjustable at the time of surgery to suit the neutral zone of each individual patient. The resistance to movement provided by the dynamic spine stabilizer 10 is adjustable pre-operatively and intra-operatively. This helps to tailor the mechanical properties of the dynamic spine stabilizer 10 to suit the compromised spine of the individual patient. The length of the dynamic spine stabilizer 10 is also adjustable intra-operatively, to suit individual patient anatomy and to achieve desired spinal posture. The dynamic spine stabilizer 10 can be re-adjusted post-operatively with a surgical procedure to adjust its central zone to accommodate a patient's altered needs.

Ball joints 36, 38 link the dynamic spine stabilizer 10 with the pedicle screws 16, 18. The junction of the dynamic spine stabilizer 10 and pedicle screws 16, 18 is free and rotationally unconstrained. Therefore, first of all, the spine is allowed all physiological motions of bending and twisting and second, the dynamic spine stabilizer 10 and the pedicle screws 16, 18 are protected from harmful bending and torsional forces, or moments. While ball joints are disclosed in accordance with a preferred embodiment of the present invention, other linking structures may be utilized without departing from the spirit of the present invention.

As there are ball joints 36, 38 at each end of the stabilizer 10, no bending moments can be transferred from the spine to the stabilizer 10. Further, it is important to recognize the only forces that act on the stabilizer 10 are those due to the forces of the springs 30, 32 within it. These forces are solely dependent upon the tension and compression of the stabilizer 10 as determined by the spinal motion. In summary, the stabilizer 10 sees only the spring forces. Irrespective of the large loads on the spine, such as when a person carries or lifts a heavy load, the loads coming to the stabilizer 10 are only the forces developed within the stabilizer 10, which are the result of spinal motion and not the result of the spinal load. The stabilizer 10 is, therefore, uniquely able to assist the spine without enduring the high loads of the spine, allowing a wide range of design options.

The loading of the pedicle screws 16, 18 in the present stabilizer 10 is also quite different from that in prior art pedicle screw fixation devices. The only load the stabilizer pedicle screws 16, 18 see is the force from the stabilizer 10. This translates into pure axial force at the ball joint-screw interface. This mechanism greatly reduces the bending moment placed onto the pedicle screws 16, 18 as compared to prior art pedicle screw fusion systems. Due to the ball joints 36, 38 the bending moment within the pedicle screws 16, 18 is zero at the ball joints 36, 38 and it increases toward the tip of the pedicle screws 16, 18. The area of pedicle screw-bone interface which often is the failure site in a typical prior art pedicle screw fixation device, is a less stressed site relative to prior art implementations, and is therefore not likely to fail. In sum, the pedicle screws 16, 18, when used in conjunction with the present invention, carry significantly less load and are placed under significantly less stress than typical pedicle screws.

Figure 1:
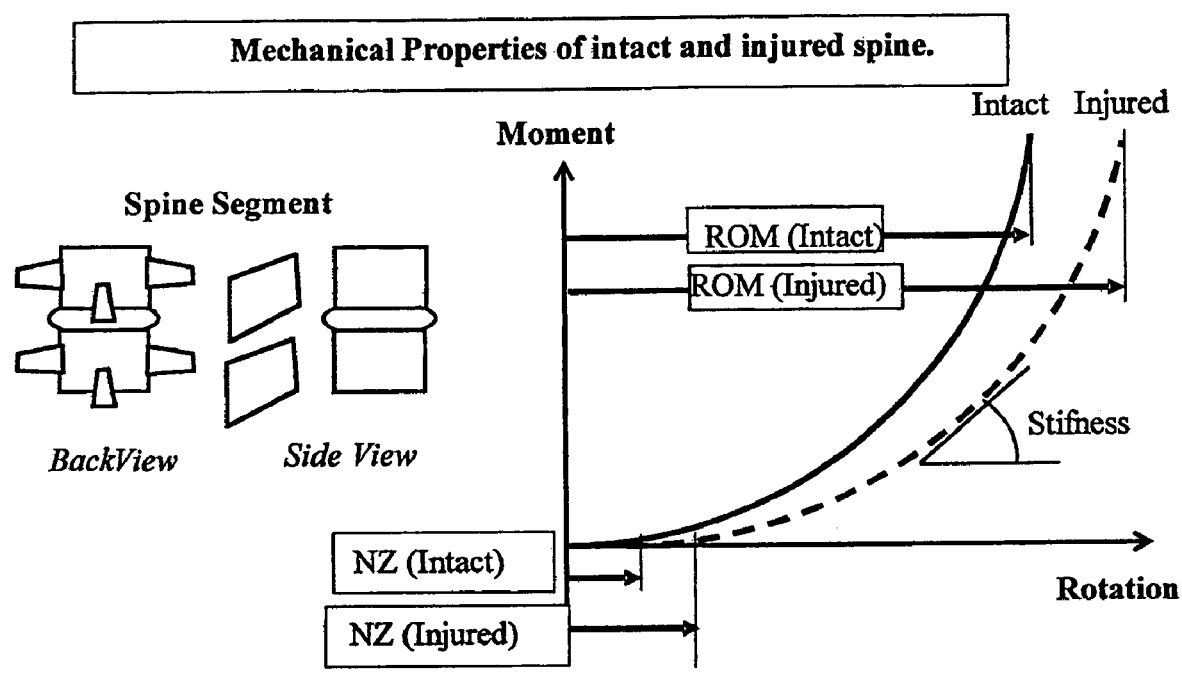
FIG. 1 is Moment-Rotation curve for a spinal segment (intact and injured), showing the low spinal stiffness within the neutral zone.

In FIG. 2, the Moment-Rotation curve for a healthy spine is shown in configurations with the present stabilizer 10. This curve shows the low resistance to movement encountered in the neutral zone of a healthy spine. However, when the spine is injured, this curve changes and the spine becomes unstable, as evidenced by the expansion of the neutral zone (see FIG. 1).

In accordance with a preferred embodiment of the present invention, people suffering from spinal injuries are best treated through the application of increased mechanical assistance in the neutral zone. As the spine moves beyond the neutral zone, the necessary mechanical assistance decreases and becomes more moderate. In particular, and with reference to FIG. 3a, the support profile contemplated in accordance with the present invention is disclosed.

Figure 3A:
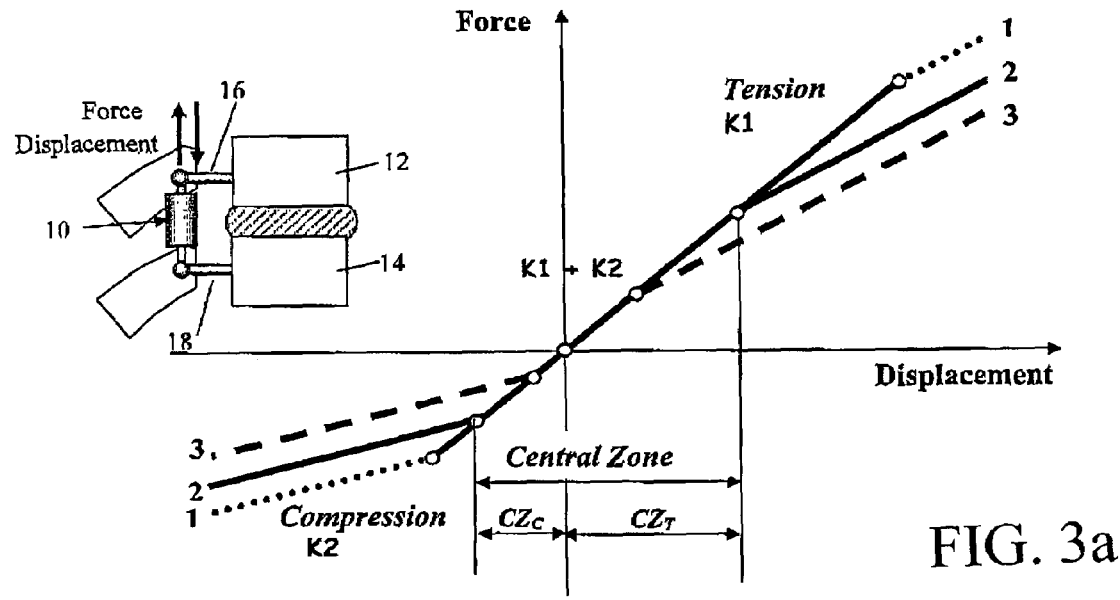
FIG. 3a is a schematic of the present invention in conjunction with a Force-Displacement curve, demonstrating the increased resistance provided within the central zone of the present dynamic spine stabilizer.
Figure 3B:
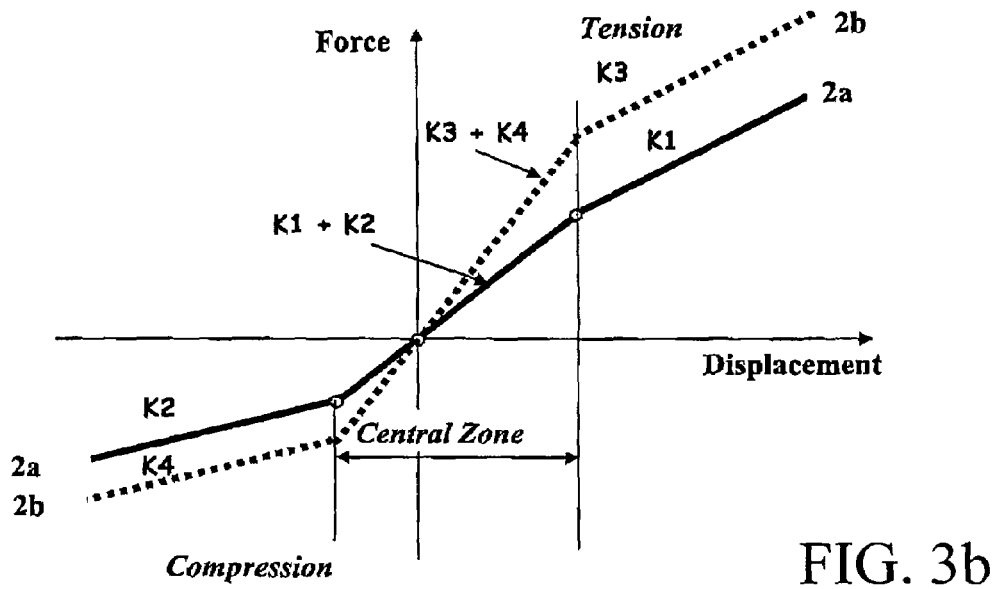
FIG. 3b is a Force-Displacement curve demonstrating the change in profile achieved through the replacement of springs.
Figure 3C:
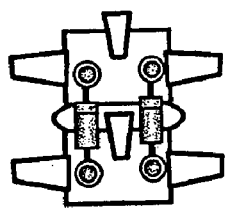
FIG. 3c is a dorsal view of the spine with a pair of stabilizers secured thereto.
Figure 3D:
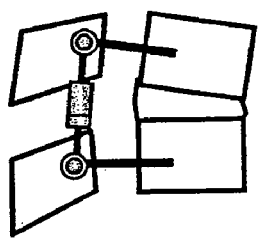
FIG. 3d is a side view showing the stabilizer in tension.
Figure 3E:
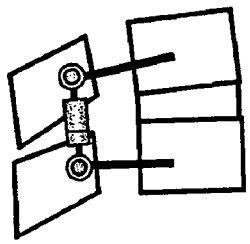
FIG. 3e is a side view showing the stabilizer in compression.

Three different profiles are shown in FIG. 3a. The disclosed profiles are merely exemplary and demonstrate the possible support requirements within the neutral zone. Profile 1 is exemplary of an individual requiring great assistance in the neutral zone and the central zone of the stabilizer is therefore increased providing a high level of resistance over a great displacement; Profile 2 is exemplary of an individual where less assistance is required in the neutral zone and the central zone of the stabilizer is therefore more moderate providing increased resistance over a more limited range of displacement; and Profile 3 is exemplary of situations where only slightly greater assistance is required in the neutral zone and the central zone of the stabilizer may therefore be decreased to provide increased resistance over even a smatter range of displacement.

As those skilled in the art will certainly appreciate, the mechanical assistance required and the range of the neutral zone will vary from individual to individual. However, the basic tenet of the present invention remains; that is, greater mechanical assistance for those individuals suffering from spinal instability is required within the individual's neutral zone. This assistance is provided in the form of greater resistance to movement provided within the neutral zone of the individual and the central zone of the dynamic spine stabilizer 10.

The dynamic spine stabilizer 10 developed in accordance with the present invention provides mechanical assistance in accordance with the disclosed support profile. Further, the present stabilizer 10 provides for adjustability via a concentric spring design.

More specifically, the dynamic spine stabilizer 10 provides assistance to the compromised spine in the form of increased resistance to movement (provided by springs in accordance with a preferred embodiment) as the spine moves from the neutral posture, in any physiological direction. As mentioned above, the Force-Displacement relationship provided by the dynamic spine stabilizer 10 in accordance with the present invention is non-linear, with greater incremental resistance around the neutral zone of the spine and central zone of the stabilizer 10, and decreasing incremental resistance beyond the central zone of the dynamic spine stabilizer 10 as the individual moves beyond the neutral zone (see FIG. 3a).

The relationship of the present stabilizer 10 to forces applied during tension and compression is further shown with reference to FIG. 3a. As discussed above, the behavior of the present stabilizer 10 is non-linear. The Load-Displacement curve has three zones: tension, central and compression. If K1 and K2 define the stiffness values in the tension and compression zones respectively, the present stabilizer is designed such that the high stiffness in the central zone is "K1+K2". Depending upon the preload of the stabilizer 10 as will be discussed below in greater detail, the width of the central zone and, therefore, the region of high stiffness can be adjusted.

Figure 4:
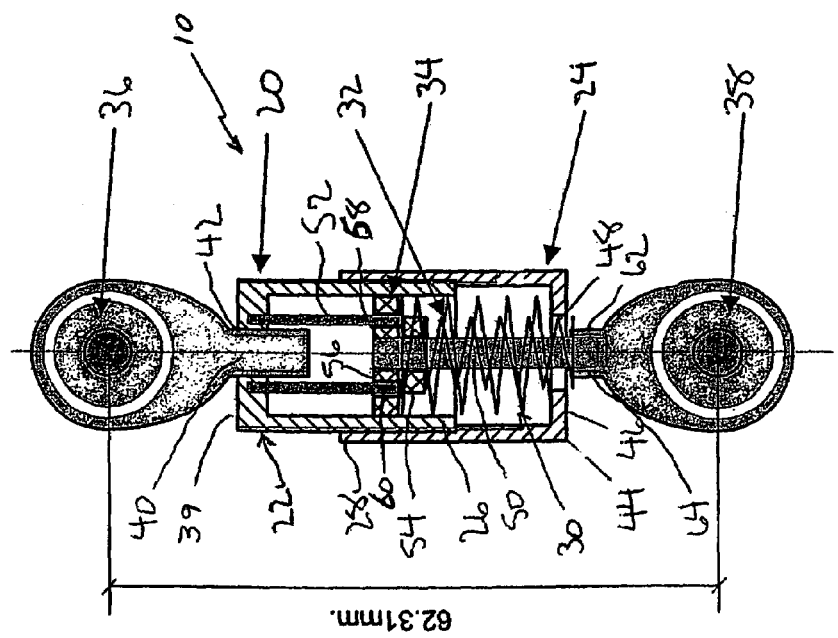
FIG. 4 is a schematic of the present dynamic spine stabilizer.

With reference to FIG. 4, a dynamic spine stabilizer 10 in accordance with the present invention is disclosed. The dynamic spine stabilizer 10 includes a support assembly in the form of a housing 20 composed of a first housing member 22 and a second housing member 24. The first housing member 22 and the second housing member 24 are telescopically connected via external threads formed upon the open end 26 of the first housing member 22 and internal threads formed upon the open end 28 of the second housing member 24. In this way, the housing 20 is completed by screwing the first housing member 22 into the second housing member 24. As such, and as will be discussed below in greater detail, the relative distance between the first housing member 22 and the second housing member 24 can be readily adjusted for the purpose of adjusting the compression of the first spring 30 and second spring 32 contained within the housing 20. Although springs are employed in accordance with a preferred embodiment of the present invention, other elastic members may be employed without departing from the spirit of the present invention. A piston assembly 34 links the first spring 30 and the second spring 32 to first and second ball joints 36, 38. The first and second ball joints 36, 38 are in turn shaped and designed for selective attachment to pedicle screws 16, 18 extending from the respective vertebrae 12, 14.

The first ball joint 36 is secured to the closed end 39 of the first housing member 22 via a threaded engagement member 40 shaped and dimensioned for coupling, with threads formed within an aperture 42 formed in the closed end 39 of the first housing member 22. In this way, the first ball joint 36 substantially closes off the closed end 39 of the first housing member 22. The length of the dynamic spine stabilizer 10 may be readily adjusted by rotating the first ball joint 36 to adjust the extent of overlap between the first housing member 22 and the engagement member 40 of the first ball joint 36. As those skilled in the art will certainly appreciate, a threaded engagement between the first housing member 22 and the engagement member 40 of the first ball joint 36 is disclosed in accordance with a preferred embodiment, although other coupling structures may be employed without departing from the spirit of the present invention.

The closed end 44 of the second housing member 24 is provided with a cap 46 having an aperture 48 formed therein. As will be discussed below in greater detail, the aperture 48 is shaped and dimensioned for the passage of a piston rod 50 from the piston assembly 34 therethrough.

The piston assembly 34 includes a piston rod 50 and retaining rods 52 that cooperate with first and second springs 30, 32. The piston rod 50 includes a stop nut 54 and an enlarged head 56 at its first end 58. The enlarged head 56 is rigidly connected to the piston rod 50 and includes guide holes 60 through which the retaining rods 52 extend during operation of the present dynamic spine stabilizer 10. As such, the enlarged head 56 is guided along the retaining rods 52 while the second ball joint 38 is moved toward and away from the first ball joint 36. As will be discussed below in greater detail, the enlarged head 56 interacts with the first spring 30 to create resistance as the dynamic spine stabilizer 10 is extended and the spine is moved in flexion.

A stop nut 54 is fit over the piston rod 50 for free movement relative thereto. However, movement of the stop nut 54 toward the first ball joint 36 is prevented by the retaining rods 52 that support the stop nut 54 and prevent the stop nut 54 from moving toward the first ball joint 36. As will be discussed below in greater detail, the stop nut 54 interacts with the second spring 32 to create resistance as the dynamic spine stabilizer 10 is compressed and the spine is moved in extension.

The second end 62 of the piston rod 50 extends from the aperture 48 at the closed end 44 of the second housing member 24, and is attached to an engagement member 64 of the second ball joint 38. The second end 62 of the piston rod 50 is coupled to the engagement member 64 of the second ball joint 38 via a threaded engagement. As those skilled in the art will certainly appreciate, a threaded engagement between the second end 62 of the piston rod 50 and the engagement member 64 of the second ball joint 38 is disclosed in accordance with a preferred embodiment, although other coupling structures may be employed without departing from the spirit of the present invention.

As briefly mentioned above, the first and second springs 30, 32 are held within the housing 20. In particular, the first spring 30 extends between the enlarged head 56 of the piston rod 50 and the cap 46 of the second housing member 24. The second spring 32 extends between the distal end of the engagement member 64 of the second ball joint 38 and the stop nut 54 of the piston rod 50. The preloaded force applied by the first and second springs 30, 32 holds the piston rod in a static position within the housing, 20, such that the piston rod is able to move during either extension or flexion of the spine.

In use, when the vertebrae 12, 14 are moved in flexion and the first ball joint 36 is drawn away from the second ball joint 38, the piston rod 50 is pulled ,within the housing 20 against the force being applied by the first spring 30. In particular, the enlarged head 56 of the piston rod 50 is moved toward the closed end 44 of the second housing member 24. This movement causes compression of the first spring 30, creating resistance to the movement of the spine. With regard to the second spring 32, the second spring 32, which is captured between stop nut 54 and second ball joint 38, extends or lengthens as a result of movement of second ball joint 38 away from first ball joint 36. As the vertebrae move in flexion within the neutral zone, the height of the second spring 32 is increased, reducing the distractive force, and in effect increasing the resistance of the device to movement. Through this mechanism, as the spine moves in flexion from the initial position both spring 30 and spring 32 resist the distraction of the device directly, either by increasing the load within the spring (i.e. first spring 30) or by decreasing the load assisting the motion (i.e. second spring 32).

However, when the spine is in extension, and the second ball joint 38 is moved toward the first ball joint 36, the engagement member 64 of the second ball joint 38 moves toward the stop nut 54, which is held is place by the retaining rods 52 as the piston rod 50 moves toward the first ball joint 36. This movement causes compression of the second spring 32 held between the engagement member 64 of the second ball joint 38 and the stop nut 54, to create resistance to the movement of the dynamic spine stabilizer 10. With regard to the first spring 30, the first spring 30 is supported between the cap 46 and the enlarged head 56, and as the vertebrae move in extension within the neutral zone, the height of the second spring 30 is increased, reducing the compressive force, and in effect increasing the resistance of the device to movement. Through this mechanism, as the spine moves in extension from the initial position both spring 32 and spring 30 resist the compression of the device directly, either by increasing the load within the spring (i.e. second spring 32) or by decreasing the load assisting the motion (i.e. first spring 30).

Based upon the use of two concentrically positioned elastic springs 30, 32 as disclosed in accordance with the present invention, an assistance (force) profile as shown in FIG. 2 is provided by the present dynamic spine stabilizer 10. That is, the first and second springs 30, 32 work in conjunction to provide a large elastic force when the dynamic spine stabilizer 10 is displaced within the central zone of the stabilizer. However, once displacement between the first ball joint 36 and the second ball joint 38 extends beyond the central zone of the stabilizer 10 and the neutral zone of the individual's spinal movement, tile incremental resistance to motion is substantially reduced as the individual no longer requires the substantial assistance needed within the neutral zone. This is accomplished by setting the central zone of the device disclosed herein. The central zone of the force displacement curve is the area of the curve which represents when both springs are acting in the device as described above. When the motion of the spine is outside the neutral zone and the correlating device elongation or compression is outside the set central zone, the spring which is elongating reaches its free length. Free length, as anybody skilled in the art will appreciate, is the length of a spring when no force is applied. In this mechanism the resistance to movement of the device outside the central zone (where both springs are acting to resist motion) is only reliant on the resistance of one spring: either spring 30 in flexion or spring 32 in extension.

As briefly discussed above, the dynamic spine stabilizer 10 is adjusted by rotation of the first housing member 22 relative to the second housing member 24. This movement changes the distance between the first housing member 22 and the second housing member 24 in a manner which ultimately changes the preload placed across the first and second springs 30, 32. This change in preload alters the resistance profile of the present dynamic spine stabilizer 10 from that shown in Profile 2 of FIG. 3a to an increase in preload (see Profile 1 of FIG. 3a) which enlarges the effective range in which the first and second springs 30, 32 act in unison. This increased width of the central zone of the stabilizer 10 correlates to higher stiffness over a larger range of motion of the spine. This effect can be reversed as evident in Profile 3 of FIG. 3a.

The present dynamic spine stabilizer 10 is attached to pedicle screws 16, 18 extending from the vertebral section requiring support. During surgical attachment of the dynamic spine stabilizer 10, the magnitude of the stabilizer's central zone can be adjusted for each individual patient, as judged by the surgeon and/or quantified by an instability measurement device. This adjustable feature of the dynamic spine stabilizer 10 is exemplified in the three explanatory profiles that have been generated in accordance with a preferred embodiment of the present invention (see FIG. 2; note the width of the device central zones).

Pre-operatively, the first and second elastic springs 30, 32 of the dynamic spine stabilizer 10 can be replaced by a different set to accommodate a wider range of spinal instabilities. As expressed in FIG. 3b, Profile 2b demonstrates the force displacement curve generated with a stiffer set of springs when compared with the curve shown in Profile 2a of FIG. 3b.

Intra-operatively, the length of the dynamic spine stabilizer 10 is adjustable by turning the engagement member 40 of the first ball joint 36 to lengthen the stabilizer 10 in order to accommodate different patient anatomies and desired spinal posture. Pre-operatively, the piston rod 50 may be replaced to accommodate an even wider range of anatomic variation.

The present dynamic spine stabilizer 10 has been tested alone for its load-displacement relationship. When applying tension, the dynamic spine stabilizer 10 demonstrated increasing resistance up to a pre-defined displacement, followed by a reduced rate of increasing resistance until the device reached its fully elongated position. When subjected to compression, the dynamic spine stabilizer 10 demonstrated increasing resistance up to a pre-defined displacement, followed by a reduced rate of increasing resistance until the device reached its fully compressed position. Therefore, the dynamic spine stabilizer 10 exhibits a load-displacement curve that is non-linear with the greatest resistance to displacement offered around the neutral posture. This behavior helps to normalize the load-displacement curve of a compromised spine.

Figure 5:
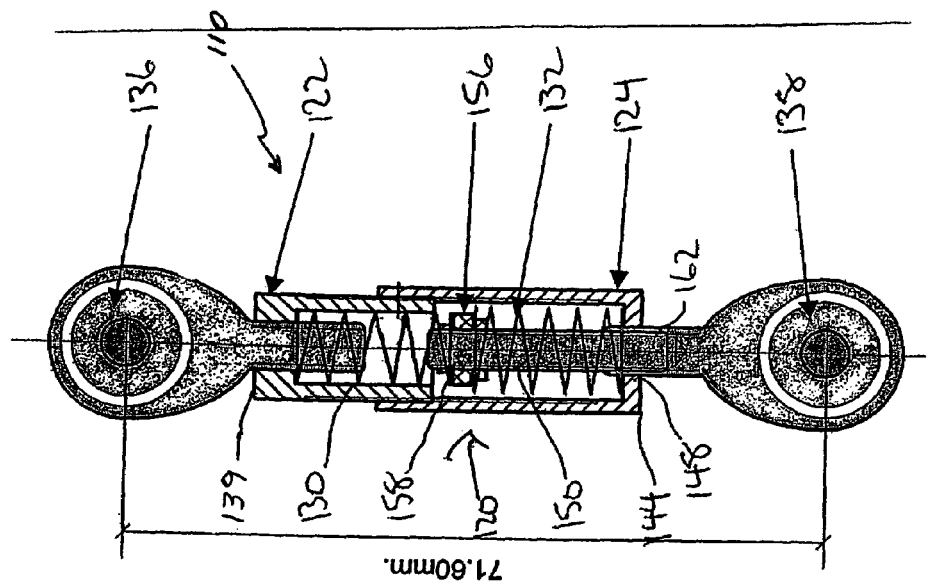
FIG. 5 is a schematic of an alternate embodiment in accordance with the present invention.

In another embodiment of the design, with reference to FIG. 5, the stabilizer 110 may be constructed with an in-line spring arrangement. In accordance with this embodiment, the housing 120 is composed of first and second housing members 122, 124 which are coupled with threads allowing for adjustability. A first ball joint 136 extends from the first housing member 122. The second housing member 124 is provided with an aperture 148 through which the second end 162 of piston rod 150 extends. The second end 162 of the piston rod 150 is attached to the second ball joint 138. The second ball joint 138 is screwed onto the piston rod 150.

The piston rod 150 includes an enlarged head 156 at its first end 158. The first and second springs 130, 132 are respectively secured between the enlarged head 156 and the closed ends 139, 144 of the first and second housing members 122, 124. In this way, the stabilizer 110 provides resistance to both expansion and compression using the same mechanical principles described for the previous embodiment.

Adjustment of the resistance profile in accordance with this alternate embodiment is achieved by rotating the first housing member 122 relative to the second housing member 124. Rotation in this way alters the central zone of high resistance provided by the stabilizer 110. As previously described one or both springs may also be exchanged to change the slope of the force-displacement curve in two or three zones respectively.

Figure 6:
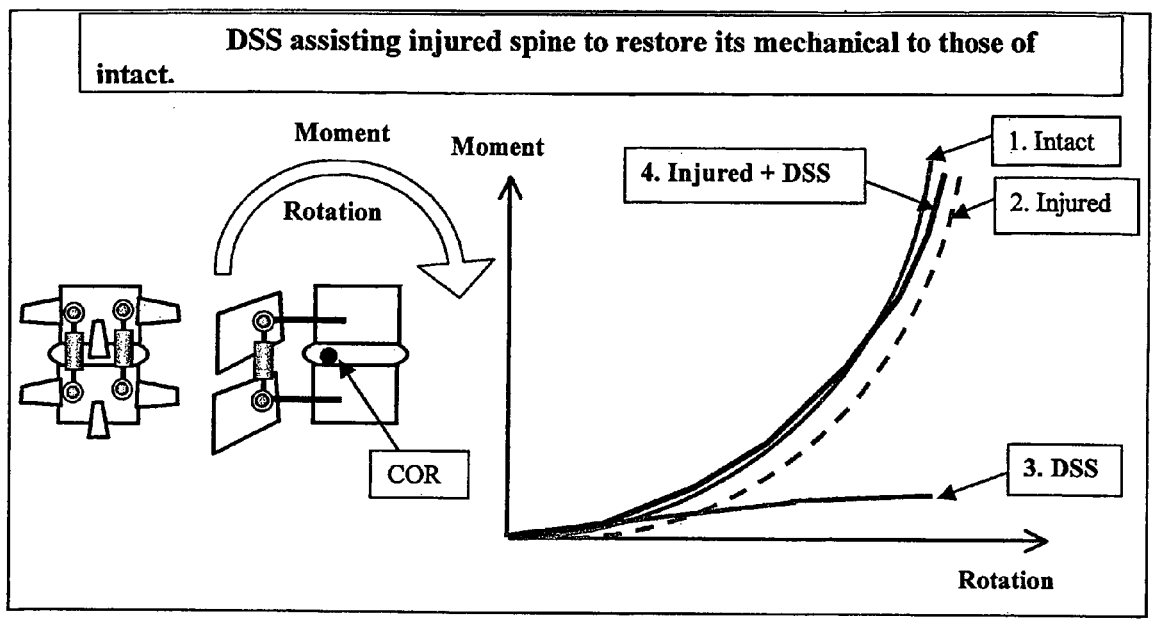
FIG. 6 is a Moment-Rotation curve demonstrating the manner in which the present stabilizer assists spinal stabilization.

To explain how the stabilizer 10, 110 assists a compromised spine (increased neutral zone) observe the moment-rotation curves (FIG. 6). Four curves are shown: 1. Intact, 2. Injured, 3. Stabilizer and, 4. Injured+Stabilizer. These are, respectively, the Moment-Rotation curves of the intact spine, injured spine, stabilizer alone, and stabilizer plus injured spine Notice that this curve is close to the intact curve. Thus, the stabilizer, which provides greater resistance to movement around the neutral posture, is ideally suited to compensate for the instability of the spine.

In addition to the dynamic spine stabilizer described above, other complementary devices are contemplated. For example, a link-device may be provided for joining the left- and right-stabilizer units to help provide additional stability in axial rotation and lateral bending. This link-device will be a supplement to the dynamic spine stabilizer. It will be applied as needed on an individual patient basis. In addition, a spinal stability measurement device may be utilized. The measurement device will quantify the stability of each spinal level at the time of surgery. This device will attach intra-operatively to a pair of adjacent spinal components at compromised and uncompromised spinal levels to measure the stability of each level. The stability measurements of the adjacent uninjured levels relative to the injured level(s) can be used to determine the appropriate adjustment of the device. Additionally, the stability measurements of the injured spinal level(s) can be used to adjust the device by referring to a tabulated database of normal uninjured spinal stabilities. The device will be simple and robust, so that the surgeon is provided with the information in the simplest possible manner under operative conditions.

The choice of spring used in accordance with the present invention to achieve the desired force profile curve is governed by the basic physical laws governing the force produced by springs. In particular, the force profile described above and shown in FIG. 3a is achieved through the unique design of the present stabilizer.

Figure 7A:
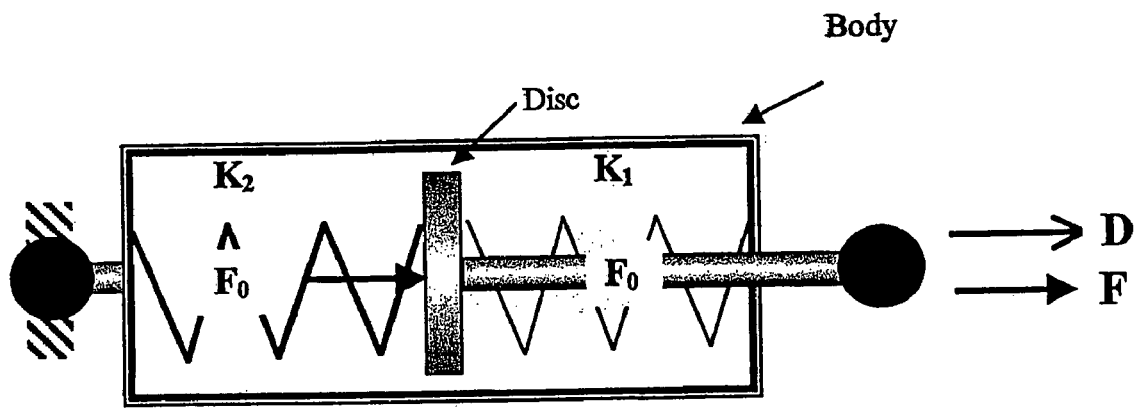
FIGS. 7a and 7b are respectively a free body diagram of the present stabilizer and a diagram representing the central zone of the present stabilizer.
Figure 7B:
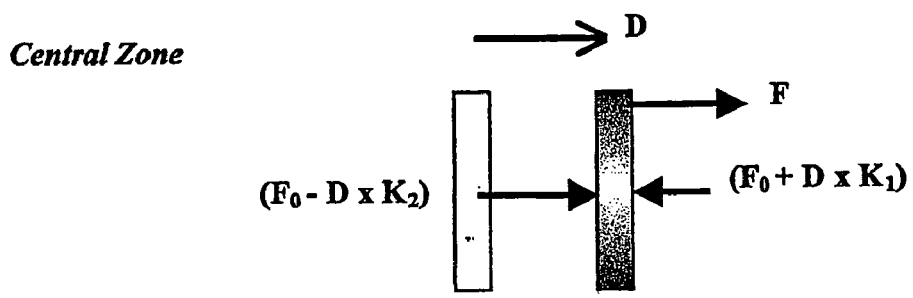
Figure 1:
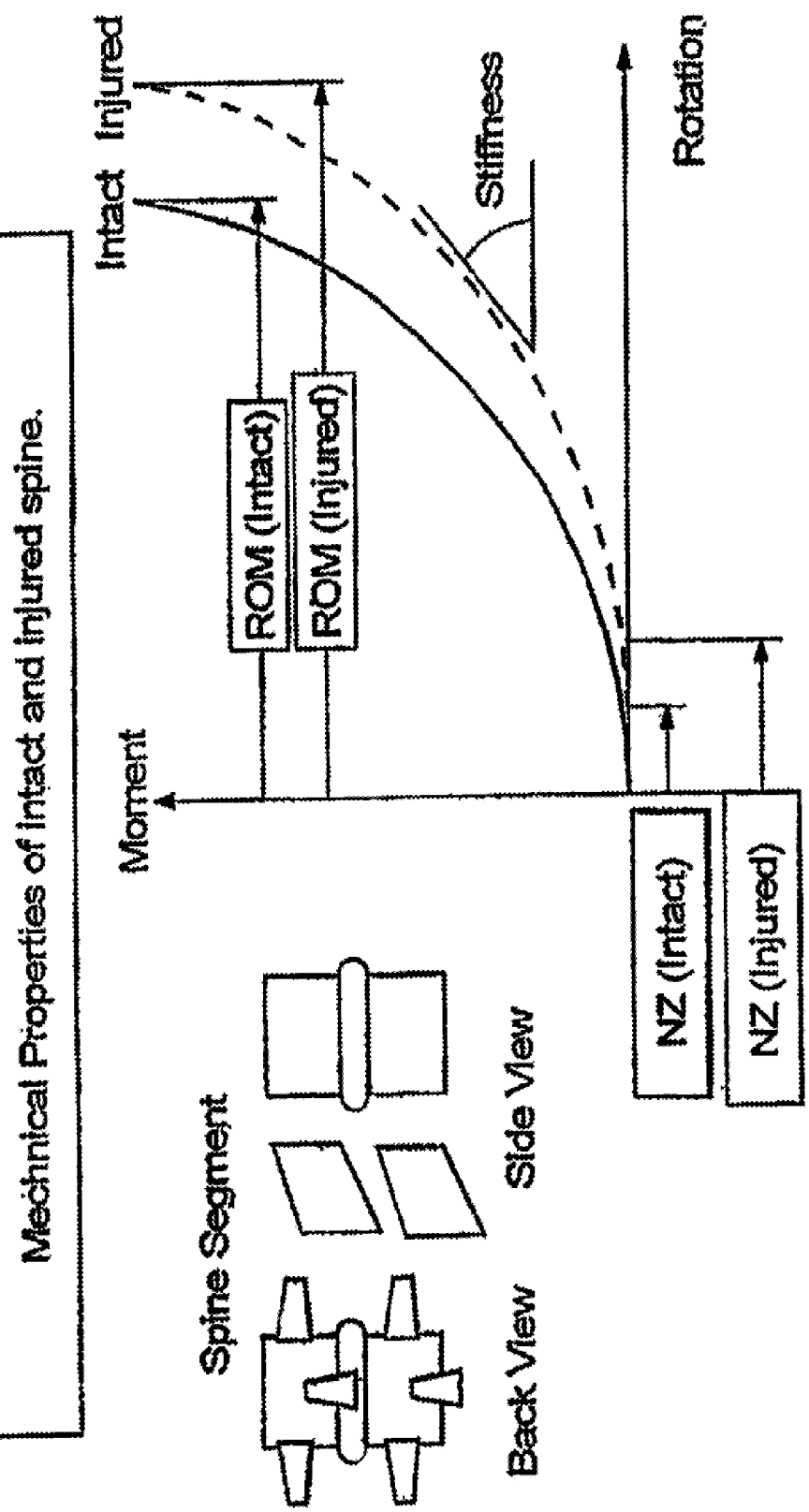
Figure 2:
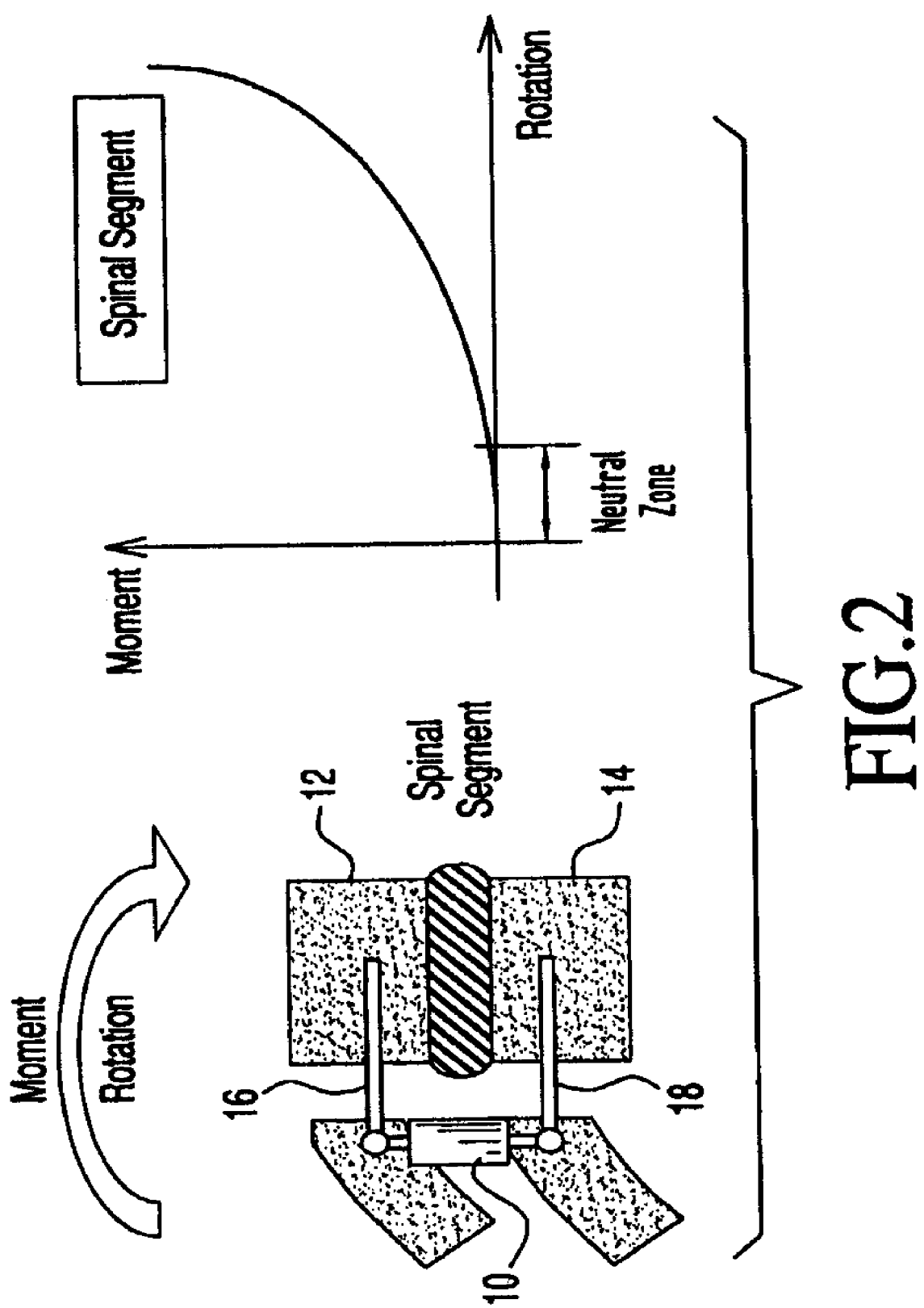
Figure 3A:
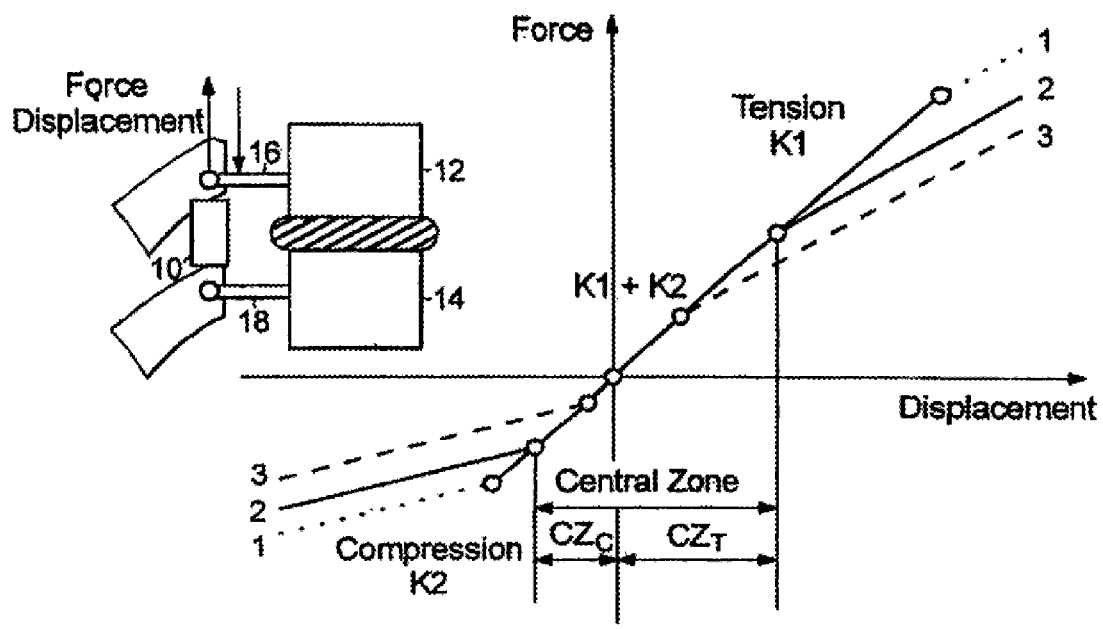
Figure 3B:
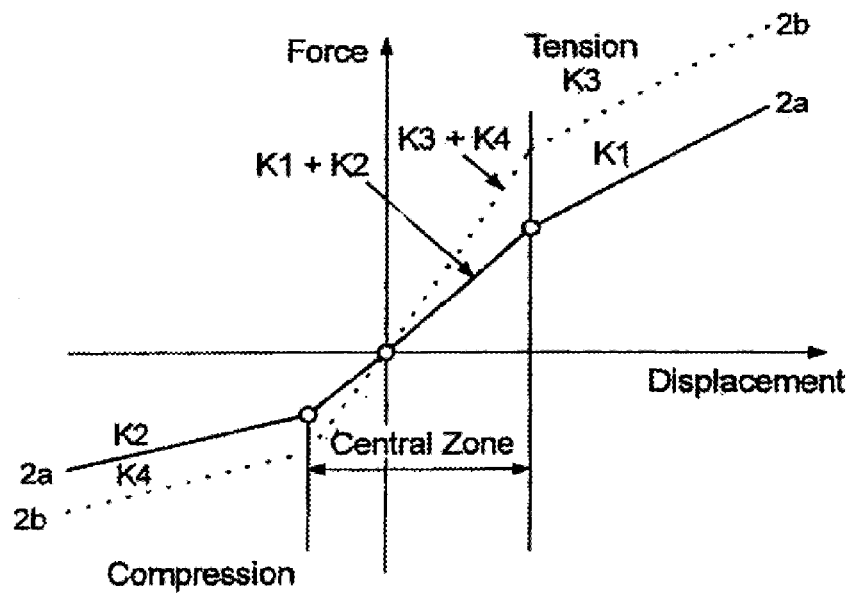
Figure 3C:
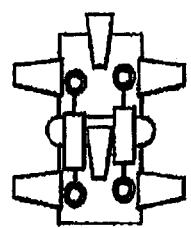
Figure 3D:
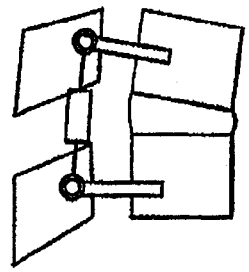
Figure 3E:
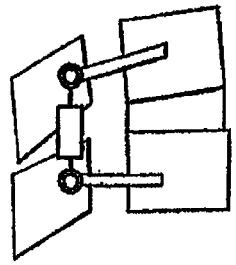
Figure 5:
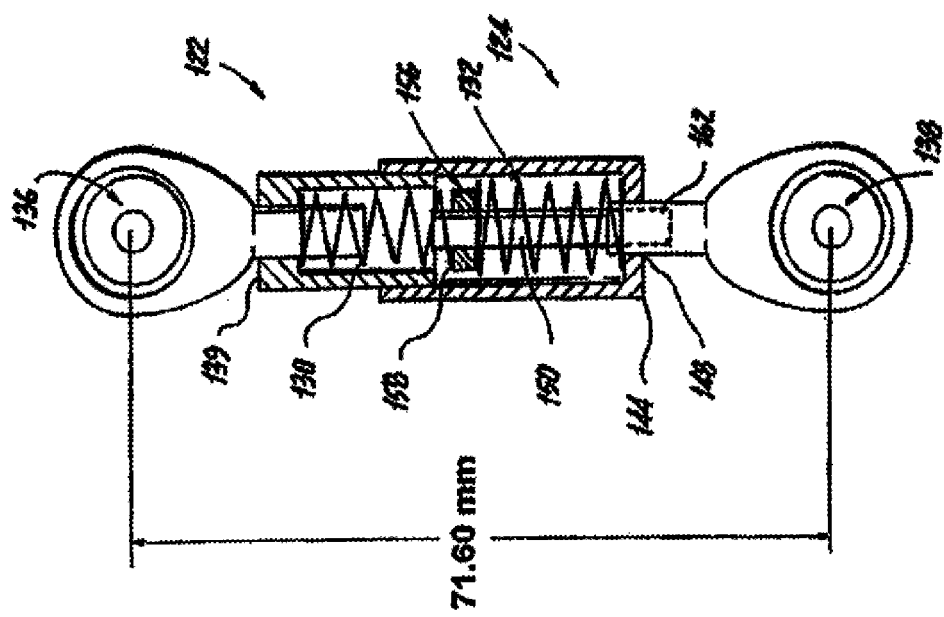
Figure 4:
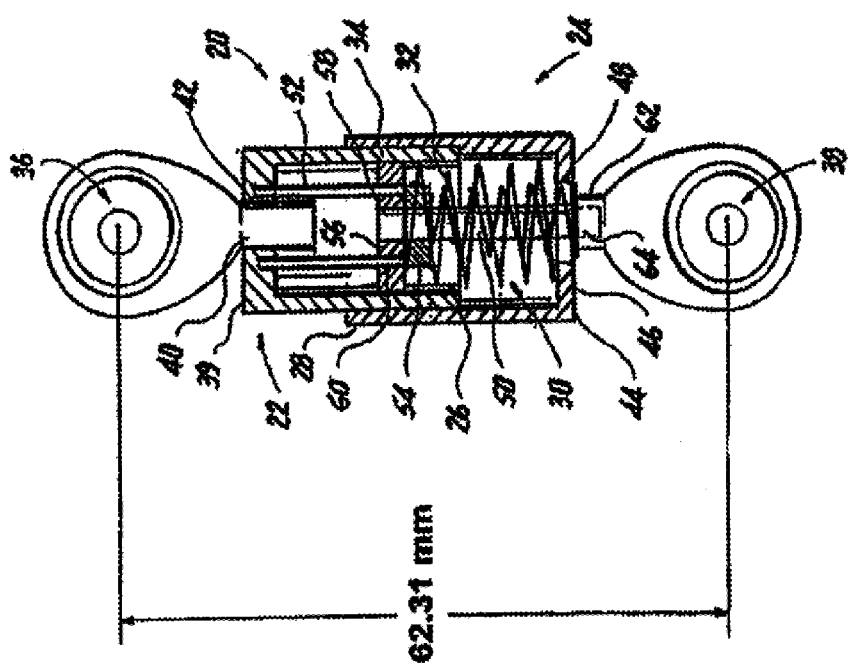
Figure 6:
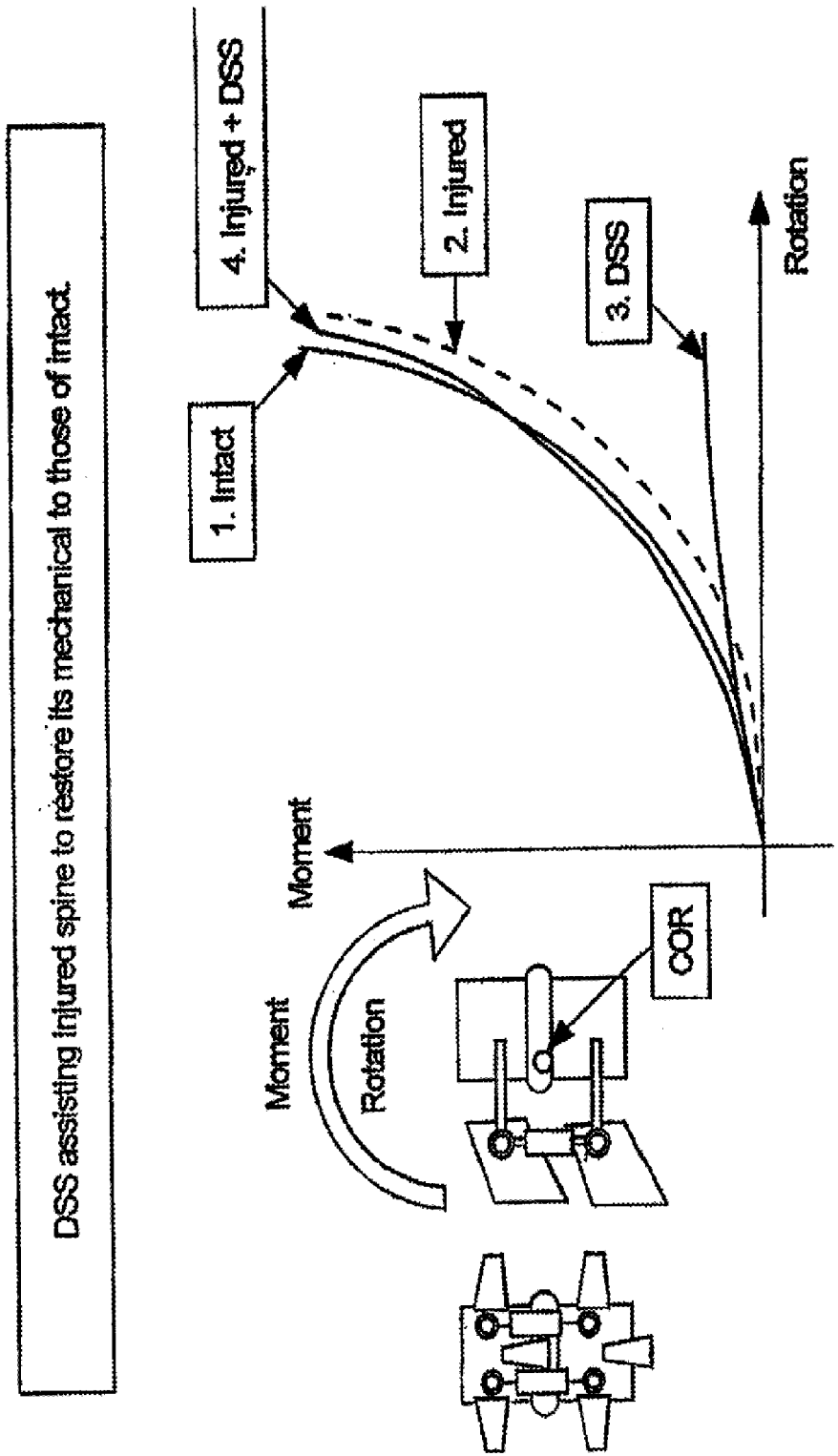
Figure 7A:
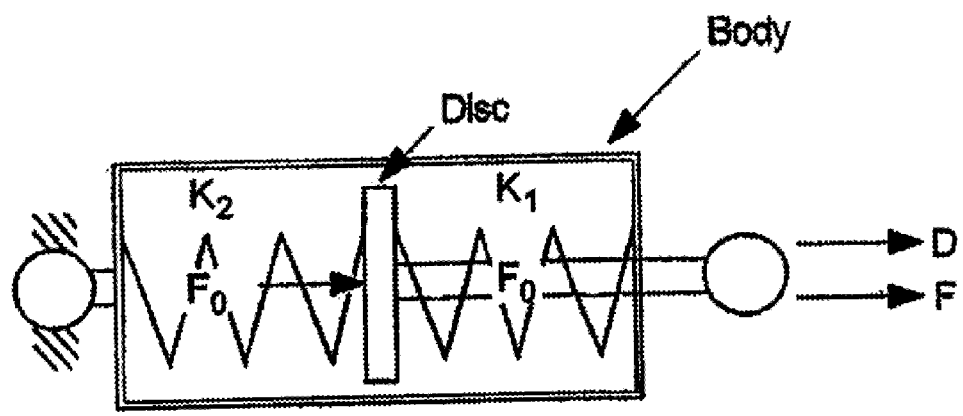
Figure 7B:
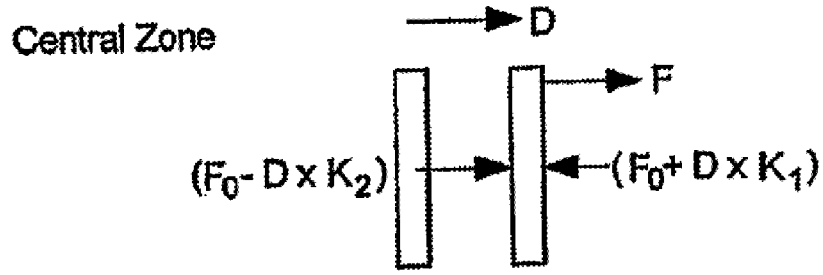

First, the stabilizer functions both in compression and tension, even through the two springs within the stabilizer are both of compression type. Second, the higher stiffness ($K_1+K_2$) provided by the stabilizer in the central zone is due to the presence of a preload. Both springs are made to work together, when the preload is present. As the stabilizer is either tensioned or compressed, the force increases in one spring and decreases in the other. When the decreasing force reaches the zero value, the spring corresponding to this force no longer functions, thus decreasing the stabilizer function, an engineering analysis, including the diagrams shown in FIGS. 7a and 7b, is presented below (the analysis specifically relates to the embodiment disclosed in FIG. 5, although those skilled in the art will appreciate the way in which it applies to all embodiments disclosed in accordance with the present invention).

$F_0$ is the preload within the stabilizer, introduced by shortening the body length of the housing as discussed above.

$K_1$ and $K_2$ are stiffness coefficients of the compression springs, active during stabilizer tensioning and compression, respectively.

F and D are respectively the force and displacement of the disc of the stabilizer with respect to the body of the stabilizer.

The sum of forces on the disc must equal zero. Therefore, $$F+(F_0-D\times K_2)-(F_0+D\times K_1)=0, \text{ and}$$

$$F=D\times(K_1+K_2).$$

With regard to the central zone (CZ) width (see FIG. 3a):
On Tension side $CZ_T$ is:

$$CZ_T=F_0/K_2.$$

On Compression side CZc is:

$$CZ_c=F_0/K_1.$$

As those skilled in the art will certainly appreciate, the concepts underlying the present invention may be applied to other medical procedures. As such, these concepts may be utilized beyond spinal treatments without departing from the spirit of the present invention.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A method for spinal stabilization, comprising the following steps: securing a dynamic stabilizer with respect to vertebrae of a spine; providing mechanical assistance in the form of resistance to a region of the spine to which the stabilizer is attached, wherein the resistance is applied such that greater mechanical assistance is provided while the spine is around its neutral zone and lesser mechanical assistance is provided while the spine bends beyond its neutral zone.

2. The method according to claim 1, wherein said step of securing a dynamic stabilizer to vertebrae of a spine includes attaching at least two pedicle screws with respect to the vertebrae.

3. The method according to claim 2, wherein ball joints couple the at least two pedicle screws to the stabilizer.

4. The method according to claim 1, wherein the resistance provided by the stabilizer is non-linear, being greatest in its central zone so as to correspond to the neutral zone of a patient.

5. The method according to claim 1, further including the step of adjusting the resistance to suit the neutral zone of a patient.

6. The method according to claim 5, wherein the step of adjusting is performed pre-operatively.

7. The method according to claim 5, wherein the step of adjusting is performed intra-operatively.

8. The method according to claim 5, wherein the step of adjusting is performed post-operatively.

9. A method for spinal stabilization, comprising:
(a) mounting a dynamic stabilizer with respect to vertebrae of a spine, said dynamic stabilizer including first and second springs;
(b) subjecting the spine to an initial range of motion, whereby the dynamic stabilizer delivers a resistive force that is based on spring resistance from said first and second springs; and
(c) subjecting the spine to a further range of motion beyond said initial range of motion, whereby the dynamic stabilizer delivers a resistive force that is based on spring resistance from only one of said first and second springs;
wherein the resistive force is applied such that greater mechanical assistance is provided while the spine is around its neutral zone and lesser mechanical assistance is provided while the spine bends beyond its neutral zone.

10. The method according to claim 9, wherein said first and second springs are subject to an initial preload.

11. The method according to claim 10, further comprising adjusting the initial preload of the first and second springs.

12. The method according to claim 11, wherein said first and second springs are positioned within a housing, and wherein said adjustment of said preload is effected by adjusting the positioning of said housing relative to at least one of said first and second springs.

13. The method according to claim 9, wherein said first and second springs are in a nested orientation.

14. The method according to claim 9, wherein said pair of springs are in an axially aligned orientation.

15. The method according to claim 9, wherein said initial range of motion corresponds to a neutral zone for said spine.

16. The method according to claim 9, further comprising:
(a) providing first and second pedicle screws;
(b) mounting said first and second pedicle screws with respect to vertebrae of the spine; and
(c) mounting the dynamic stabilizer with respect to said first and second pedicle screws.

17. The method according to claim 16, wherein a ball joint is positioned between said dynamic stabilizer and said first pedicle screw.

18. The method according to claim 16, wherein first and second ball joints are positioned between said dynamic stabilizer and said first and second pedicle screws, respectively.

19. The method according to claim 9, wherein said dynamic stabilizer demonstrates increasing resistance within said initial range of motion, and further wherein said dynamic stabilizer demonstrates a reduced rate of increasing resistance within said further range of motion.

* * * * *

UNITED STATES PATENT AND TRADEMARK OFFICE
CERTIFICATE OF CORRECTION

| | |
|---|---|
| PATENT NO. | : 7,029,475 B2 |
| APPLICATION NO. | : 10/835109 |
| DATED | : April 18, 2006 |
| INVENTOR(S) | : Manohar M. Panjabi |

It is certified that error appears in the above-identified patent and that said Letters Patent is hereby corrected as shown below:

The Title Page, showing an illustrative figure, should be deleted and substitute therefor the attached title page.

Delete drawings sheets 1, 3, 4, 5, 6, 7 and substitute therefor the drawing sheets, consisting of figs. 1-7b as shown on the attached page.

Signed and Sealed this

Twenty-seventh Day of May, 2008

JON W. DUDAS
*Director of the United States Patent and Trademark Office*

(12) United States Patent
Panjabi

(10) Patent No.: US 7,029,475 B2
(45) Date of Patent: Apr. 18, 2006

(54) SPINAL STABILIZATION METHOD

(75) Inventor: Manohar M. Panjabi, New Haven, CT (US)

(73) Assignee: Yale University, New Haven, CT (US)

(*) Notice: Subject to any disclaimer, the term of this patent is extended or adjusted under 35 U.S.C. 154(b) by 0 days.

(21) Appl. No.: 10/835,109

(22) Filed: Apr. 30, 2004

(65) Prior Publication Data
US 2004/0236329 A1 Nov. 25, 2004

Related U.S. Application Data

(60) Provisional application No. 60/506,724, filed on Sep. 30, 2003, provisional application No. 60/467,414, filed on May 2, 2003.

(51) Int. Cl.
A61B 17/56 (2006.01)

(52) U.S. Cl. .......................................... 606/61

(58) Field of Classification Search .............. 606/61, 606/60; 623/17.11, 17.12, 17.13, 17.14, 623/17.15, 17.16; 128/898
See application file for complete search history.

(56) References Cited

U.S. PATENT DOCUMENTS

| | | |
|---|---|---|
| 2,733,596 A | 2/1956 | Painter |
| 4,328,960 A | 5/1982 | Handke et al. |
| 4,352,514 A | 10/1982 | Orima |
| 4,558,852 A | 12/1985 | Steiner et al. |
| 4,650,167 A | 3/1987 | Steiner et al. |
| 4,743,260 A | 5/1988 | Burton |
| 4,759,769 A * | 7/1988 | Hedman et al. ......... 623/17.13 |
| 5,034,011 A | 7/1991 | Howland |
| 5,174,551 A | 12/1992 | Mintgen |
| 5,180,393 A | 1/1993 | Commarmond |
| 5,291,901 A | 3/1994 | Graf |
| 5,329,933 A | 7/1994 | Graf |
| 5,375,823 A * | 12/1994 | Navas ............... 623/17.15 |
| 5,415,661 A | 5/1995 | Holmes |
| 5,423,816 A | 6/1995 | Lin |
| 5,480,401 A * | 1/1996 | Navas ............... 606/61 |
| 5,505,118 A | 4/1996 | Amesen et al. |
| 5,540,688 A | 7/1996 | Navas |
| 5,562,737 A | 10/1996 | Graf |
| 5,653,680 A | 8/1997 | Cruz |
| 5,672,175 A | 9/1997 | Martin |

(Continued)

FOREIGN PATENT DOCUMENTS

AU 654740 B 11/1994

(Continued)

OTHER PUBLICATIONS

Keller, Tony S. et al., "Force-deformation response of the lumbar spine: a sagittal plane model of . . . ", Clinical Biomechanics 17 (2002) 185-196.

(Continued)

*Primary Examiner*—Pedro Philogene
(74) *Attorney, Agent, or Firm*—McCarter & English, LLP

(57) ABSTRACT

A dynamic spine stabilizer moves under the control of spinal motion providing increased mechanical support within a central zone corresponding substantially to the neutral zone of the injured spine. The dynamic spine stabilizer includes a support assembly and a resistance assembly associated with the support assembly. The resistance assembly generates greater increase in mechanical force during movement within the central zone and lesser increase in mechanical force during movement beyond the central zone. A method for using the stabilizer is also disclosed.

19 Claims, 7 Drawing Sheets

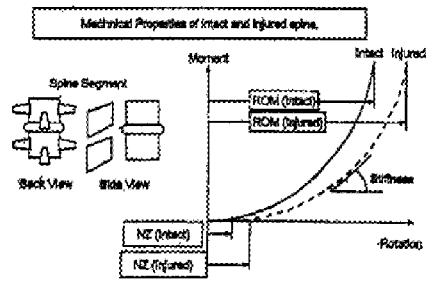
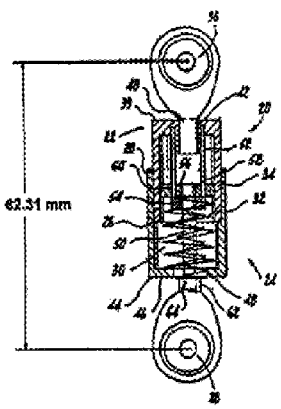

DSS in Tension

DSS in Tension

UNITED STATES PATENT AND TRADEMARK OFFICE
CERTIFICATE OF CORRECTION

PATENT NO.       : 7,029,475 B2                           Page 1 of 1
APPLICATION NO.  : 10/835109
DATED            : April 18, 2006
INVENTOR(S)      : Manohar M. Panjabi It is certified that error appears in the above-identified patent and that said Letters Patent is hereby corrected as shown below:

In the specification:

Insert at col. 1, line 3 -- STATEMENT REGARDING FEDERALLY SPONSORED RESEARCH

This invention was made with government support under Grant No. AR045452 awarded by the National Institute of Health. The government has certain rights in the invention. --

Signed and Sealed this
Sixth Day of December, 2011

David J. Kappos
*Director of the United States Patent and Trademark Office*